United States Patent [19]

Yamashita et al.

[11] 4,158,545
[45] Jun. 19, 1979

[54] AUTOMATIC CHEMICAL ANALYZING METHOD AND APPARATUS

[75] Inventors: Katsuji Yamashita; Hiroshi Umetsu; Kazuyoshi Heguri, all of Katsuta; Kasumi Yoshida, Mito, all of Japan

[73] Assignee: Hitachi, Ltd., Japan

[21] Appl. No.: 834,902

[22] Filed: Sep. 20, 1977

[30] Foreign Application Priority Data

Sep. 22, 1976 [JP] Japan ............................ 51-114226

[51] Int. Cl.² .......................... G01N 1/14; G01N 1/18
[52] U.S. Cl. ............................ 23/230 R; 73/425.4 R; 364/497; 422/67; 422/68
[58] Field of Search ................ 23/230 R, 253 R, 259; 364/497; 73/425.4 R

[56] References Cited
U.S. PATENT DOCUMENTS

| 3,728,080 | 4/1973 | Moran | 23/253 R |
| 3,748,044 | 7/1973 | Liston | 23/253 R |
| 4,058,367 | 11/1977 | Gilford | 23/253 R |

OTHER PUBLICATIONS

SMAC: The Computer Controlled Analyzer, presented at the Technicon International Congress, Jun. 12–14, 1972 in N.Y., by Amar et al.

Primary Examiner—R. E. Serwin
Attorney, Agent, or Firm—Craig and Antonelli

[57] ABSTRACT

In an automatic chemical analyzing method and apparatus in which a plurality of samples each added with a reagent are discretely transported through a reaction line and subjected to a reaction during the transportation for optical measurement to generate measured signals and to process them, the samples to be analyzed are grouped into a plurality of sample groups each including a plurality of samples which are to be measured with respect to the same test items, which are previously stored for each sample group in a memory of a central control unit. The samples are divided by a number corresponding to the number of test items and successively fed to the reaction line one by one in sample groups, and, at the time of change of the sample group receiving the analysis, test items corresponding to a new sample group are read from the memory to carry out a chemical analysis for the samples in each sample group according to the read test items.

16 Claims, 5 Drawing Figures

AUTOMATIC CHEMICAL ANALYZING METHOD AND APPARATUS

LIST OF PRIOR ART REFERENCE (37 CFR 1.56(a))

The following references are cited to show the state of the art:
U.S. Pat. No. 3,728,080, Moran et al, Apr. 17, 1973, 23-259
SMAC: The computer Controlled Analyzer, presented at the Technicon International Congress, June 12-14, 1972 in New York, by Amar et al.

BACKGROUND OF THE INVENTION

The present invention relates to an automatic chemical analyzing method and apparatus, and more particularly to a multi-item automatic chemical analyzing method and apparatus suitably adapted to measure serum or the like by the photometry.

Many automatic chemical analyzing apparatus in current use, and in particular automatic chemical analyzing apparatus used for clinical tests in hospitals are based on a method in which a certain amount of samples to be measured is extracted into a reaction tube with a reagent added thereto to cause a chemical reaction to make a colorimetric measurement by the use of a spectrophotometer and to provide measurement results which are fed out in terms of concentration of analyzed compositions or in terms of a particular unit. Such an automatic chemical analyzing appatatus has simultaneous test items which differ in number depending upon its model, and many apparatus can analyze one to twenty items with an apparatus with two test items called a two-channel automatic chemical analyzers and an apparatus with six test items called a six-channel automatic analyzers.

The test items treated in a biochemical field at a clinical laboratory amount to several tens kinds of items. However, the test items which are treated in daily routine works and subjected to a frequent test is not so great in number, for example, ten or more. These test items are common with a number of samples, whose treatment is made automatic by the above-mentioned automatic chemical analyzer. In this respect, for the automatic analysis of twelve test items there are required six two-channel automatic chemical analyzer, two six-channel automatic chemical analyzer or one twelve-channel automatic analyzer. Alternatively, the twelve items are sometimes measured, for example, in such a manner that the two-channel automatic chemical analyzer is switched at each end of analysis of two items, or the six-channel chemical analyzing apparatus at each end of analysis of six items. Recently, a number of samples are analyzed at the clinical labortory, where the automatic operation is required for the samples with the result of frequent use of a multi-channel automatic chemical analyzer, for example, such as a sixteen-channel automatic chemical analyzer.

In the above-mentioned prior art, a plurality of two-channel or six-channel automatic chemical analyzers can be used without any item change. For that reason, if a required number of apparatus are installed, they are operated at very poor efficiency with the disadvantageous idling operation of expensive apparatus since the samples are not so great in number for the respective automatic chemical analyzers except for great hospitals, and since the measurements can be completed shortly a day. When one apparatus is used with the items changed, the item changing operation is very sophisticated with much time consumed because of the necessity of changing a number of accessories. This often causes the degradation of efficiency and the consumption of a great amount of reagent at the time of changing the item. For example, the use of the sixteen-channel automatic chemical analyzer allows the simultaneous analysis of a sixteen items and the analysis of almost all of the items requiring the automatic operation without troubles and with very great analyzing capability. However, usual samples, it individually observed, need no test of all of the sixteen items. The ordered test item depends upon the sample, but a number, of samples generally require the measurement with respect to only several items. In this respect, the sixteen-channel automatic chemical analyzing apparatus carries out the analysis of unnecessary that items, and wastes the excessive analyzing reagent in that degree. Recently, a multichannel automatic chemical analyzer is provided with a function of selecting any item to analyze only the necessary test items for each sample for the purpose of eliminating the above-mentioned waste of the reagent and the degradation of efficiency due to the item changing operations. In this case also, an operator must supply the analyzer with information relating to the test items for each sample with the result of the extremely great labor.

An analyzer is also known which includes only one reaction line (meaning a path along which reaction tubes are arranged in a line or a pipe through which samples spaced by bubbles pass) but can make a multi-item (multi-component) measurement. Such a known one-line automatic chemical analyzer is of a type in which each of the samples are successively analyzed in terms of a plurality of specific items, or a type in which the same reaction line is used and all associated samples are first analyzed in terms of one item and then in terms of another item after the end of analysis of the one item. The analyzer of the former type is applicable only to the measurement of a sample such as urine which has common items to be measured. The analyzer of the latter type, on the other hand, has the drawback that the samples must be rearranged at the time of changing the test item with another depending upon the necessity of test of the changed item. It is difficult to make such rearrangement automatic. Further, in the latter analyzer, it takes more time to obtain results about all the test items of one sample if the test items increase in number with respect to the individual samples. Further, the measurement initiation must disadvantageously be delayed until samples having the same test items amount to a certain number because the samples must be rearranged in a sophisticated manner at each time of changing the items.

SUMMARY OF THE INVENTION

It is therefore an object of the present invention to provide an automatic chemical analyzing method and apparatus in which each sample can be analyzed in terms of a plurality of items and in which samples having different test items are analyzed in such a manner that the test items are automatically changed while continuing the chemical analysis in terms of test items corresponding to the new samples.

In accordance with the present invention, this object can be achieved in such a manner that samples are grouped into a plurality of sample groups each including a plurality of samples which are to be analyzed with respect to the same test items, and successively fed in each sample group to a reaction line, and that test items for each sample group are previously stored and automatically changed each time that the sample group fed to the reaction line changes.

In accordance with a preferred embodiment of the present invention, item selection means is provided which includes a plurality of item selection switches disposed on an operation panel. The test items for each sample group are stored in a computer memory by operating these item selection switches, and a combination of the test items are automatically changed under computer control by sensing a change occurring each time that the sample group fed to the reaction line changes. In one embodiment of the present invention, the item selection means comprises the switches disposed on the operation panel, but may comprise a card or tape without being limited thereto.

The above-mentioned and other objects and features of the present invention will be apparatus from the following description in conjunction with the drawings.

DESCRIPTION OF THE PREFERRED EMBODIMENT

The present embodiment relates to a twelve-channel automatic chemical analyzer which, as a whole, includes a sampler for feeder samples, a pipetting system for pipetting the samples and reagents in amount, a reaction system for effecting the reaction of the sample and reagent, a photometric detecting unit, and a central control unit for controlling and monitoring the data processing and the whole apparatus.

Figure 1:
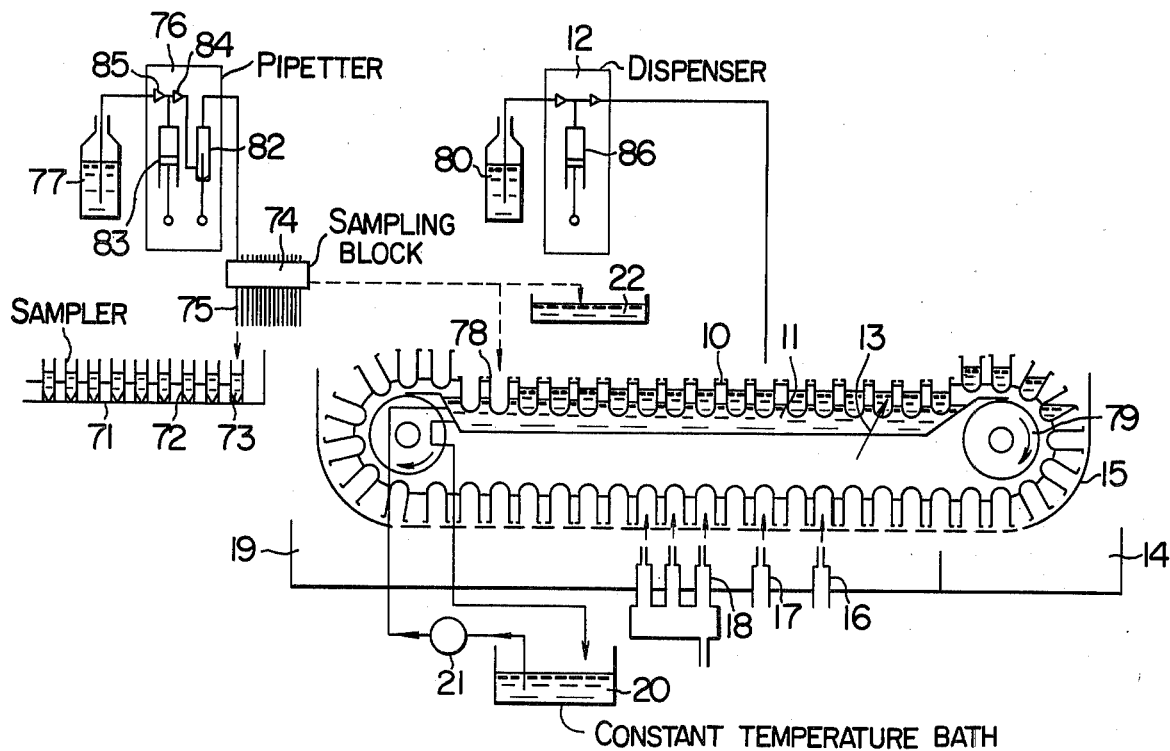
FIG. 1 is a schematic view of an arrangement showing a sampler, weighing system and reaction system according to one embodiment of the present invention.

In the following, the operational principle will be described in conjunction with the drawings in which FIG. 1 is an illustrative view showing an arrangement including the sampler, the pipetting and reaction systems of the present invention.

In FIG. 1, a sampler 71 is adapted to successively transport a number of sample tubes 72 flexibly coupled to each other in a line to a predetermined sampling station. Each of the sample tubes is contained with a sample. Samples 73 are grouped into a plurality of samples each having the same test items, and the samples belonging to each group are received in a train of sample tubes 72 so that they may be arranged successively with such groups arranged in a longitudinal train. At a boundary between the groups there is provided a special tube having a configuration different from the other sample tubes, for example, such as a tube provided with an annular projection, to sense the boundary by detecting the special configuration of the tube.

A sampling block 74 is provided with twelve nozzles 75 which are moved downwardly independently of each other on the basis of an instruction from the central control unit. Each of the nozzles is respectively connected to a pipetter 76. The pipetter 76 are twelve in number, although not shown. Each pipetter includes a micro-syringe 82 and a quantitative pump 83 each having a plunger, which is driven by an air cylinder or cam mechanism operated according to an instruction from the central control unit. The pipeter further includes check valves 84, 85. The sampling block 74 is moved horizontally to a predetermined position by a pulse motor operated according to an instruction from the central control unit. When the sample 73 in the sample tube 72 at the sampling station is pumped by the nozzle 75, the sampling block 74 is moved so that one of the twelve nozzles may be positioned directly above the sampling station. The nozzle is then lowered into the sample tube 72, and the plunger of the micro-syringe 82 is driven to pump a certain amount of samples 73. At the same time, the quantitative pump 83 is operated to pump a certain amount of reagents in a reagent bottle. After the nozzle 75 introduced into the sample tube has been raised to its original position, the sampling block 74 is moved to the right in FIG. 1 and stopped at a predetermined position, where the nozzle is introduced into a reaction tube 78 and discharges the previously pumped sample together with the reagent into the reaction tube 78. After the discharge, the nozzle is washed at a washing bath 22.

The reaction tube 78 is intermittently moved within a constant temperature water bath 11 by means of a chain 10 operated by sprockets 79, and, if necessary, it is added with a reagent 80 necessary for reaction by means of a dispenser 12. The apparatus is provided with the necessary number of dispensers 12 each including a fixed quantity shifting pump 86 operated according to the instruction from the central control unit. The sample which has reacted within the reaction tube 78 reaches a photometer section 13, in which the reaction sample is subjected to an absorbance measurement by a method to be described later in FIG. 2. The sample subjected to the reaction, after the end of the measurement, is moved out of the constant temperature water bath 11 and turned over for drain at the end of the reaction system. The sample turned over for drain drops into a measured sample drain tank 14 and is introduced together into a suitable reservoir (not shown). The reaction tube 78 is further moved along a guide 15 for purposes of washing by city water from a nozzle 16, washing by distilled water from a nozzle 17 and hot blast drying from a nozzle 18, and then again turned over into a noninverted state for re-use at the pipetting station. The washing drainage drops out of the guide 15 together into a washing drainage tank 19 and is drained off by a drain tube (not shown). The water in the constant temperature water bath 11 is circulated through a constant temperature bath 20 by a pump 21.

The apparatus according to the embodiment of the present invention includes such a single reaction line, and the analysis is carried out longitudinally in terms of multi-terms on the single reaction line for substantially simultaneous analysis is terms of the multi-items with the above-mentioned operations intermittently performed at a certain time interval. In this sense, it may be called a single line-multichannel method. The principle of the single line-multichannel method will be apparent from the description of a photometric detecting unit in FIG. 2. It is of course that a plurality of similar reaction lines may be provided.

Figure 2:
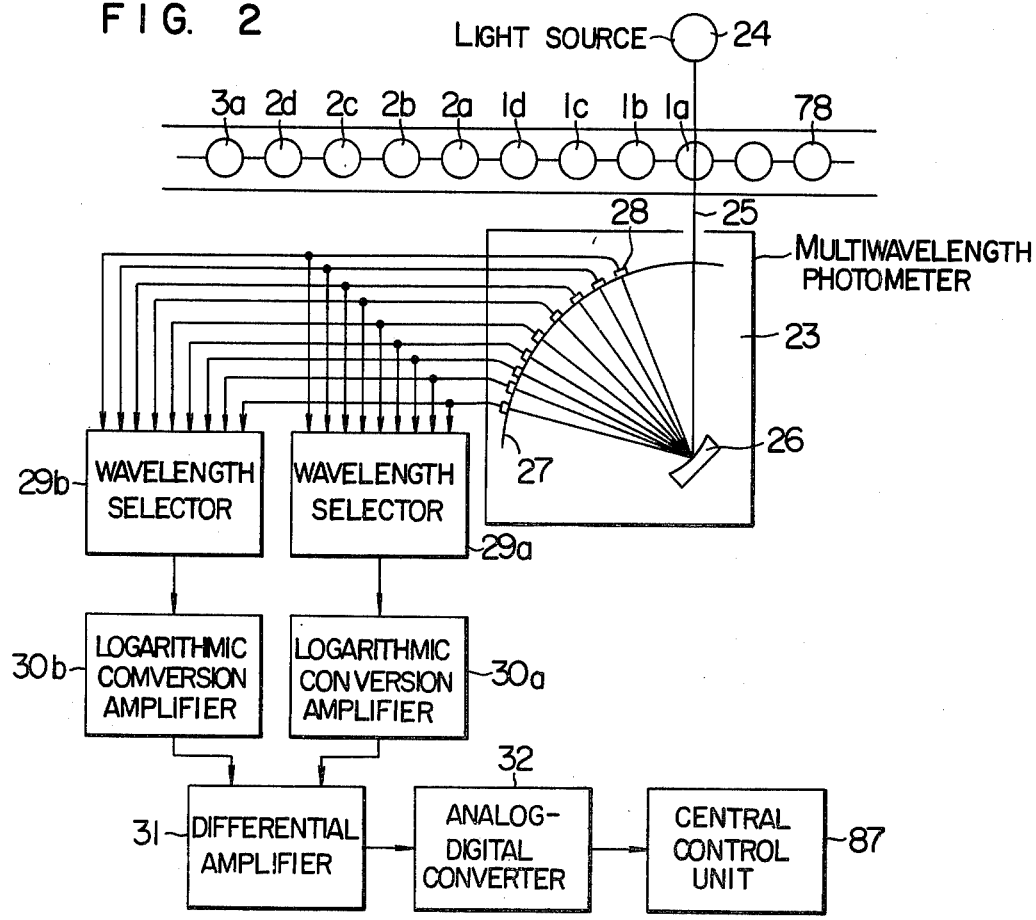
FIG. 2 is an illustrative view showing a photometric detecting unit.

FIG. 2 is an illustrative view of a photometric detecting unit according to the present invention wherein each sample is subjected to a simultaneous four-item analysis (actually measured intermittently with a delay but referred to as "simultaneous" for convenience), and a sample No. 1 is measured in terms of a test item a. In FIG. 2, a train of transparent a reaction tubes 78 is moved intermittently within the constant temperature water bath, and stopped temporally at a position where the sample 1a subjected to the reaction receives a light beam 25 from a light source 24 such as a tungsten lamp, and the light beam 25 is subjected to a light absorption by the reaction sample 1a. The light beam 25 is incident on a concaved diffraction grating 26 of a multiwavelength photometer 23 and diffused in spectra with the respective spectrum collected on a Rowland circle 27. A plurality of sensors 28 are provided on the Rowland circle 27 depending upon the wavelength to be measured. The outputs from the sensors 28 are applied to two wavelength selectors 29a, 29b for wavelength measurement. The wavelength selectors include a switching circuit switched according to an instruction from the central control unit, and select a signal from the sensor which has detected the wavelength corresponding to the test item a to supply it to the following logarithmic conversion amplifiers 30a, 30b, respectively. A differential amplifier 31 detects the difference of outputs from the two logarithmic conversion amplifier 30a, 30b and feeds it to an analog-digital converter 32. An output from the analog-digital converter 32 is sent to a central control unit 87 for data processing.

At the next timing, the reaction tube 78 containing a sample 1b subjected to the reaction is moved to the light beam station and receives the photometric measurement similar to the above with the exception that the wavelength to be measured is selected by the wavelength selectors 29a, 29b in accordance with a test item b. These operations are similarly made for samples 1c, 1d. The following samples 2a, 2b, 2c, 2d subjected to the reaction are intended to measure a sample No. 2 in terms of the test items a, b, c, d, and they receive the similar treatment as the sample No. 1. The above photometric method is called a direct photometric method because the reaction tube 78 receives a direct photometric operation without using any flow cell. In this respect, the measurement principle of this embodiment can be called a single line-multichannel-direct photometric method. In the above-mentioned method, it will be apparent that the twelve simultaneous test items can be accepted, and in principle more items can also be accepted.

Figure 3:
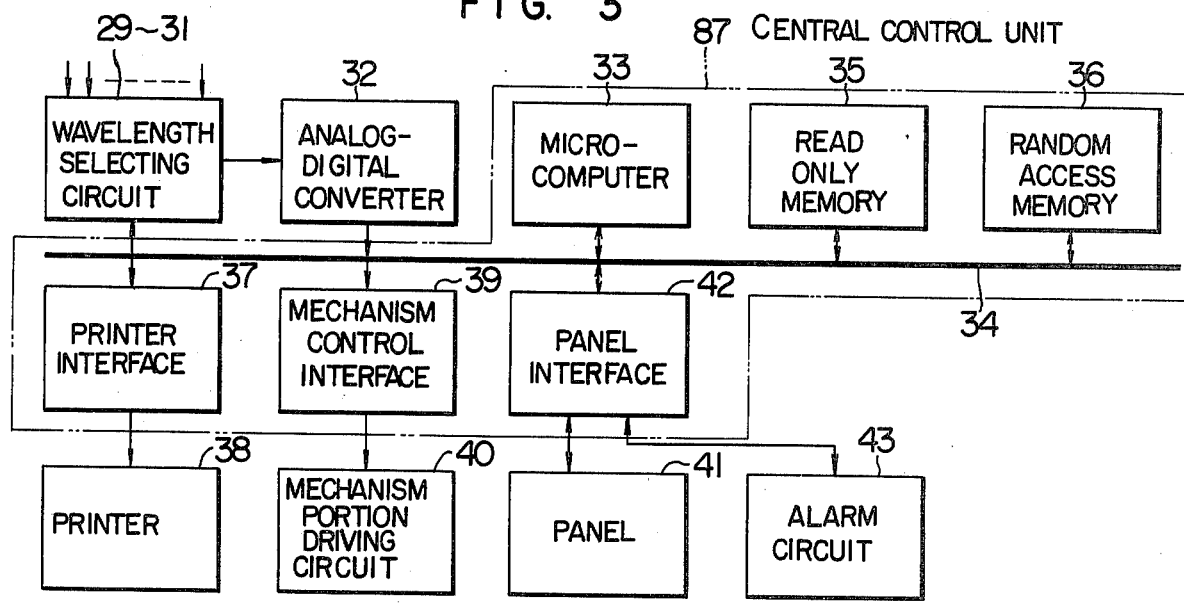
FIG. 3 is an illustrative view showing a connection of a central control unit in the embodiment of FIG. 1 to the whole analyzing apparatus.

FIG. 3 shows an arrangement of the central control unit 87 in this embodiment and its connections to portions of the analyzer. The central control unit includes a microcomputer 33 at its center and functional portions, which are connected by a bus line 34. The programs for operating each portion of the apparatus such as the sampler 71, sampling block 74, pipetter 76, sprockets 79, dispenser 12, etc. are stored in a read-only memory 35. A random access memory 36 serves to perform data processings and store variable intermation. The measured data selected by the wavelength selecting circuit 29 to 31 are fed from the analog-digital converter 32. The measured data are processed according to the test items by the microcomputer 33 in accordance with the program, stored in the memory 36, and then read in the previously programmed order with the measurement results printed by a printer 38 through a printer interface 37.

Measuring conditions such as the test items for each sample group and operation timings of each working portion of the automatic chemical analyzer corresponding to each item are stored through a panel interface 42 in the random access memory 36 by operating a keyboard on a panel 41 made integral with the apparatus. During the analysis, the measuring conditions stored in the memory 36 are monitored by the program stored in the read-only memory 35 to produce an instruction for driving each working portion when the operation of the automatic chemical analyzer coincides with the operation condition of the working portion.

The operational timing of each mechanism portion of the apparatus is, therefore, controlled by an instruction supplied to a mechanism portion driving circuit 40 through a mechanism control interface 39.

An alarm circuit 43 examines the working conditions of the whole apparatus and informs the microcomputer 33 of the occurrence of any disorder through the panel interface 42. The microcomputer 33 acts appropriately according to the information and displays the content of the disorder on the panel 41.

Figure 4:
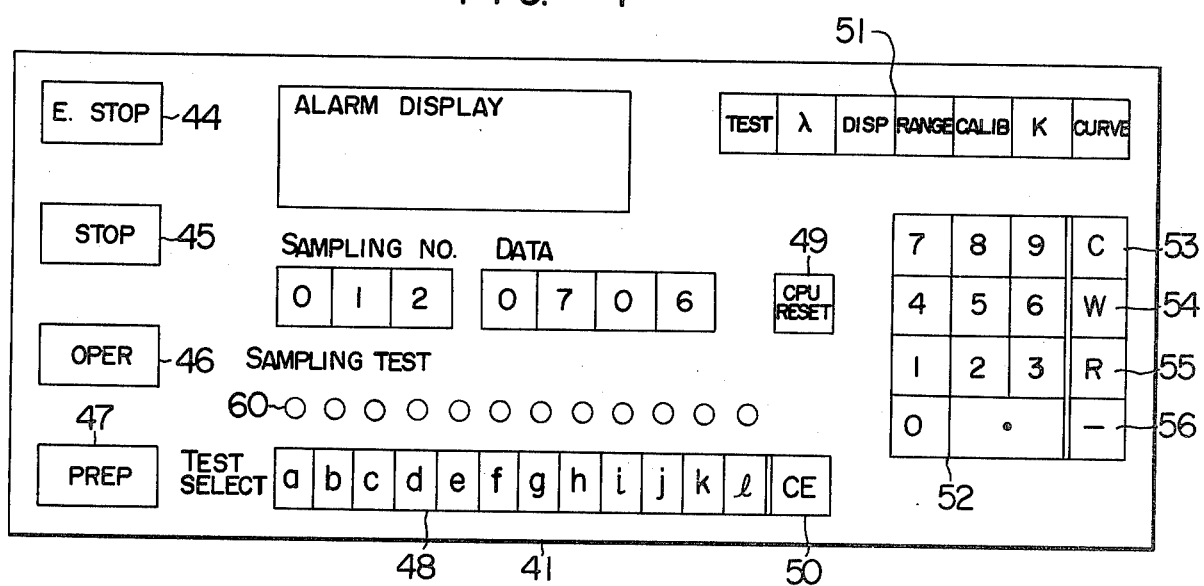
FIG. 4 is a plan view showing a control panel used in one embodiment of the present invention.

FIG. 4 shows a control panel provided on the automatic chemical analyzer according to the present invention. Switches 44 to 50 are lighted push button switches used for daily operations, and switches 51 to 56 are push button switches for altering set conditions, and not used for the daily operations. At first, the description will be made about the daily operation. The connection of the power supply to the apparatus causes the lamp of the stop switch 45 to be turned on, and the central control unit presets the initial condition according to the program and waits the operation of an operator.

The analysis operation is initiated in such a manner that the operator sets to the sampler 71 the first sample group required for analysis, for example, in terms of items a, c, e, and then pushes necessary ones of the twelve test item selection switches 48, a, b, c, ... k, l (a plurality of switches can be simultaneously selected in any combination) as well as the operation switch 46. The random access memory 36 comprises test item words each including bits corresponding to the test item selection switches 48 in one-to-one relation with only the bits corresponding to the pushed switches being inverted from "0" to "1". At the same time, the pushed switch is lit, while the operation switch 46 is lit darkly. The central control unit receives the input information and operates, before the measurement, to turn on the heater for feeding a hot blast to the nozzle 18. After confirming that the measuring condition is ready, the operation switch 46 is lit to initiate the analysis operation of the automatic chemical analyzer. At the same time as at the initiation of the analysis operation, the test item selected by the test item selection switch 48 is displayed by turning on the display lamp 60 for the test item subjected to the sampling, and the analysis item selection switch 48 is then extinguished. Thereafter, the analyzer continues the analysis operations according to the method described with reference to FIGS. 1 to 3. In other words, reference is made to the information stored in the random access memory according to the program in the read-only memory 35, and the central control unit produces an instruction for operating each working portion of the apparatus to control the analysis operation of the whole apparatus on the basis of the instructions.

After the setting of the test items for one group has been completed, the operation pushes the selection switch 48 corresponding to items to be tested or test items such as items b, d, e, h to be analyzed for another sample group after the extinguishment of the previously selected switches 48, and further pushes the operation switch 46. This causes the central control unit to be supplied with an input for selecting the test items for the sample group following the analysis of the preceding sample group. Thus, the analysis operation of the first sample group is followed by that of the second sample group.

Figure 5:
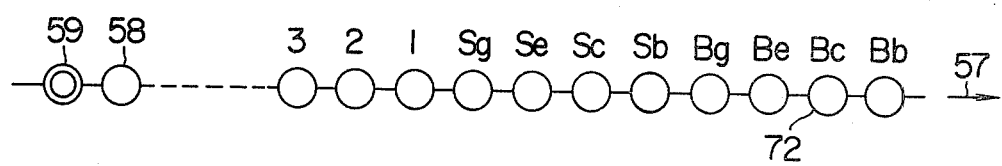
FIG. 5 is an illustrative view showing an example of arrangement of samples in a reaction line.

The automatic calibration of the apparatus will next be described. FIG. 5 shows the arrangement of samples when items b, c, e, g are selected as the the simultaneous test item. Assume that a train of samples advance in the direction of arrow 57 in FIG. 5 on the sampler 71 in FIG. 1. The first four sample tubes 72 are respectively filled with a solution of zero concentration (generally called "blank", for which distilled water is used) for the test items, and the following four sample tubes 72 are filled with standard solutions $S_b$, $S_c$, $S_e$, $S_g$ corresponding thereto, respectively. These solutions are followed by samples to be measured which are arranged in the order of sample numbers. The values of measurement for blanks $B_b$, $B_c$, $B_e$, $B_g$ are stored in the random access memory 36 in terms of absorbance, and a concentration coefficient $A_b$ is found by $$A_b = \frac{\text{(concentration of the standard solution for the test item } b)}{\text{(measured value for the } S_b) - \text{(measured value for the } B_b)}$$

at the time when the standard solutions $S_b$, $S_c$, $S_e$, $S_g$ have been measured. Concentration coefficients $A_c$, $A_e$, $A_g$ of the other test items are found out similarly. It is to be noted that the concentrations of the standard solutions are previously stored in the memory 36. The thus found coefficients are also stored in the memory 36. This accomplishes the automatic calibration for the apparatus with respect to the test items b, c, e, g. The analysis results of the following sample No. 1 with respect to the four items are obtained in terms of concentration values $C_{lb}$, $C_{lc}$, $C_{le}$, $C_{lg}$, $$C_{lb} = A_b(X_{lb} - B_b)$$

$$C_{lc} = A_c(X_{lc} - B_c)$$

$$C_{le} = A_e(X_{le} - B_e)$$

$$C_{lg} = A_g(X_{lg} - B_g)$$

where $X_{lb}$, $X_{lc}$, $X_{le}$, $X_{lg}$ are the measured values for the respective reaction samples. This applies for the analysis of the following samples.

Thus, the reaction line includes thereon the blanks and the standard samples which precede a train of samples to be tested and which corresponds in number to the test items selected for the sample group. The train of samples on the reaction line comprises the same number of reaction tubes or sample sections as the number of items selected for one sample, and the same number of following samples.

At the clinical laboratory, on the other hand, there are usually other sample groups such as second, third, . . . sample groups which have their test items selected differently from the above. In such case, in the present embodiment, the sample train of the first sample group as shown in FIG. 5 is followed by a sample train of th second sample group in a similar manner to that as described in FIG. 5. The test item required for the second sample group is again selected by the test item selection switch 48, and the operation switch 46 is then pushed. When the sampling for the last sample 58 in the first sample group is completed by the previously mentioned operations, and a special tube 59 indicating the boundary of the sample groups arrives at the sampling station, the sampler 71 senses it and informs the central control unit, which changes the sampling condition with that for the second sample group to continue the sampling of the following samples. In contrast to the other tubes, the special tube 59 is formed with an annular projection, which closes a switch to sense the boundary of the sample group when the tube 59 reaches the sample station.

In this operation, similarly as mentioned above, the test item selected by the test item selection switch 48 is also displayed by turning on the lamp 60 for displaying the test item subjected to the sampling. The test items and analysis conditions required for the control of the whole apparatus are automatically changed by reading next test item words in the memory 36. The analysis for the third sammple group is similarly prepared in such a manner that its test item is selected and the automatic test item change is performed at the boundary of the sample group similarly as mentioned above. The alternation of the test item is to change the wavelength to be measured, the sampling block, the control for the pippetter and dispenser, the content of operational processing, the print order and the like. These are all monitored and controlled by the central control unit. A switch 50 serves to once clear the test item selection switches 48 when they are operated erroneously. A switch 49 serves to again start the apparatus when it suffers from troubles and comes to a stop and after its function is restored.

The description will next be made with respect to the switches 51 to 56 not used for daily operations, but for a case in which the set condition of the analyzer must be changed. The switches 51 are lighted switches for selecting the kinds of input information. The switches 52 are key board switches used for numerical portions of the input information. The switches 53 to 56 are used to delete, write and read the input information and to select the negative sign, respectively.

The test items for each sample group and the measuring condition for each item are stored in the memory 36 by operating the keys on the operation panel 41. Each test item includes the item itself and further information for controlling the wavelength to be measured, sampling block, pipetter, dispenser, control signals, etc.. The twelve test item selection switches 48 a to l allows the storing of the information about twelve items in the memory 36. The information is tabled and stored in the memory 36 not in terms of the test items but in terms of information. The test item will now be described by way of an example. The test item is thirty in number as shown in Table 1, and twelve of the items can be suitably selected.

Table 1

| Code | Test item |
| --- | --- |
| 1 | Alkaline Phosphatase |
| 2 | Glutamic Oxalocetic Transaminase |
| 3 | Glutamic Pyruvic Transaminase |
| . | |
| . | |
| . | |

Table 1-continued

| Code | Test item |
|------|-----------|
| . | . |
| . | . |
| . | . |
| 30 | Creatine Phosphokinase |

These items are successively provided with code numbers 1 to 30. Information about necessary items is successively stored in the memory 36 in items by operating the test item selection switches 48 on the panel 41 and the keys on the keyboard 52. If, for example, the test item code No. 3 is selected by the button a, code No. 10 by the button 6, . . . and code No. 25 by the button l, then a table such as shown in Table 2 is stored in the memory 36.

Table 2

| Word order | Code No. |
|------------|----------|
| 1 | 0 0 0 0 0 0 1 1 ( 3) |
| 2 | 0 0 0 0 1 0 1 0 (10) |
| . | . |
| . | . |
| . | . |
| . | . |
| 12 | 0 0 0 1 1 0 0 1 (25) |

Other information is similarly tabled.

The description will next be made with respect to the operation of changing only one of the set test items with another item.

(1) One of the test item selection switches 48 is pushed which corresponds to the test item intended for alternation.

(2) The "Test" switch of the switches 51 is pushed. The code number of the test item to be newly set is fed by the keyboard switches 52. The switch 54 for writing input information is pushed to write new information in the selected word on the table in the memory 36. The input of the analyzing method for the newly set test item is fed in terms of numbers by the keyboard switches 52. In this embodiment, a fifteen-minute analyzing method, thirty-minute analyzing method, rate assay method, analyzing method required for the sample blanks and analyzing method required to correct a calibration curve deviation are respectively identified by numbers 0, 1, 2, 4, 8. This allows the alternation of content of predetermined word on the table for the analyzing method.

(3) The input with respect to a print order for measurement results of the newly set items is fed by the keyboard switches 52, and the switch 54 is pushed to alter a portion of contents on the table about the print order.

(4) The "λ" switch of the switches 51 is pushed. The inputs of two measured wavelengths of the newly set test items are fed in digits of respective double figures, total four figures by the keyboard switches 52, and the switch 54 is pushed to alter a portion of contents on a wavelength table. In this embodiment, twelve wavelengths to be measured can be selected, and respectively numbered with 1 to 12.

(5) The "DISP" switch of the switches 51 is pushed. The information about what dispenser at what position on the reaction line should be discharged is fed in digit of respective double figures, total four digits by the keyboard switches 52, and the switch 54 is pushed to alter a portion of contents on a dispenser table. In the present embodiment, sixteen dispensers are provided, which are numbered with 1 to 16, respectively. Further, the reaction line is equally divided into sixty one stations numbered with 0 to 60 with the sampling station numbered with zero and the measuring station with 60.

(6) The "RANGE" switch of the switches 51 is pushed. The input with respect to the lower limit of the normal range for the newly set test item is fed by the keyboard switches 52, and the switch 54 is then pushed. The input for the upper limit of the normal range is fed, and the switch 54 is then pushed. The upper and lower limits are respectively contained in separate tables, whose contents are partially altered.

(7) The "CALIB" switch of the switches 51 is pushed. The input with respect to the concentration of standard solution for the newly set test item is fed, and the switch 54 is pushed to partially alter the content on its table.

(8) If the rate assay method is selected in the above operation (2), then the "K" switch of the switches 51 is pushed to feed a K-factor by the keyboard switches 52, and the switch 54 is pushed to alter a portion of contents on a K-table. The K-factor is an output converting coefficient in the rate assay method, and is calculated logically.

(9) If a correction with respect to the calibration curve showing a relation between the measured signal and the concentration is needed in the newly set test item, then the "CURVE" switch of the switches 51 is pushed to feed calibration curve data, and the switch 54 is pushed to supply a calibration curve table with the new data. In this embodiment, a polygonal approximation with six line elements is employed, and the above operations are repeated six times.

The above-mentioned operations accomplish the alternation of the set conditions for the apparatus and the setting of quite new test items. The input information due to the above operations is stored in the memory 36, and all the measuring conditions are then determined only by operating the test item selection switches 48 and making reference to the memory 36. According to the present embodiment, the automatic chemical analyzing apparatus provided with the central control unit for controlling the operations of each portion and processing the measurement results includes central control unit input switches which are disposed on the operation panel provided on the analyzing apparatus and which serve to alter the test items selected by the item selection switches with other test items.

It is necessary that the information with respect to the twelve items should again be fed in the memory at the time of connection of the apparatus to the power supply when the contents on the table in the memory are made volatile at the time of disconnection from the power supply. This operation is very complicated, so that a non-volatile memory is preferably used. Further, a plurality of cards including tables with respect to the twelve items with each table containing different items from each other may be prepared to write the table in the memory 36 only by inserting the card containing its table. The card may be replaced by a tape.

The features according to the embodiments of the present invention are as follows:

(1) Any plurality of items can be analyzed depending upon samples without any troublesome rearrangement of the samples and without any feeding of information with respect to test items for each sample with the result of improvement in operational efficiency.

(2) No rearrangement of the samples is needed at the time of alternation of the test items.

(3) A plurality of test items which are displayed on the operation panel and whose measuring condition is stored in the central control unit can be selected in any combination, so that the analyzer is provided with a function which matches the function of an analyzer with a number of reaction lines even if it includes only one line. Thus an economic analyzer can be provided.

(4) The analysis results of a plurality of test items for the same samples can all be obtained in a short time.

(5) The test items combined according to a sample group can be automatically changed in sample groups without the conventional time loss or waste of reagent at the time of alteration of the items.

(6) The test items can be increased or decreased in number, so that wasteful items can be reduced with the result of improvement in rate of operation.

(7) The items within the test item group displayed on the operation panel can be altered, so that an application range can be expanded to a great extent.

(8) The provision of the operation panel on the analyzing apparatus improves operational efficiency.

In the above-mentioned embodiment, the description has been made with respect to one reaction line, but it will be apparent that two or more reaction lines can be provided. Instead of the above-mentioned single line-multichannel-direct photometric method, a multi-line-multichannel method with reaction lines corresponding in number to simultaneous test items may be employed using flow cells.

In the above-mentioned embodiment, the test items for the second sample group is selected during the analysis of the first sample group, but it will be apparent that the test items for the third, fourth, . . . sample groups can be selected at this time or the test items for all the sample groups can be selected before the initiation of analysis. This requires a slightly excessive memory in the central control unit and provides no substantial change in comparison to the present embodiment.

Other than the above-mentioned embodiment, the following modification can be concepted. It will now be assumed that the kinds of sample groups remain unchanged every day in a so-called daily routine work at the clinical laboratory with the test items made constant for the respective sample groups. In such case, any plurality of test items can be selected not by pushing the test item selection switches 48 individually, but by previously determining the combinations of the plurality of test items, for example, defining switches A, B, C as the switch A being for selecting the combination of test items a, b, c, d, e, f, switch B for selecting the combination of test items g, h, i, j, and switch C for selecting the combination of test items k, l, and only by pushing the switch A, B or C. In the above-mentioned conditon, it is further possible without any substantial modification to feed inputs about a plurality of combinations of the test items with the above switches A, B, C omitted and to change them automatically every time that the sample group is changed.

As described above, the present invention provides an automatic chemical analyzer in which the analysis is made by selecting a plurality of test items depending upon samples without any troublesome rearrangement of the samples even if the test items are altered during operation, and in which sophisticated operations can be reduced, but never the less the simplification of its structure and inexpensiveness can be achieved in comparison with the conventional apparatus in which the information with respect to the test items is fed for each sample.

We claim:

1. An automatic chemical analyzing method comprising the steps of:

successively transporting samples one by one in groups to a sampling station, said samples being grouped into a plurality of sample groups, each sample group including a plurality of samples which are to be analyzed with respect to the same test items;

successively feeding these transported samples, with each sample divided into a number of portions corresponding to the number of test items for the sample group which includes the sample, with a reagent to a reaction line;

storing the test items for each sample group in a memory of a central control unit for controlling the operation of an analyzing system in accordance with each test item prior to the feeding of the first sample of each sample group to the reaction line;

discretely transporting through said reaction line the portions of the samples fed to said reaction line, respectively;

photometrically measuring the portions of the samples subjected to a reaction during the transportation through said reaction line; and reading the test items for the sample group to be next analyzed from said memory in the central control unit to control the operation of the analyzing system in accordance with these test items when the sample group fed to said reaction line is altered.

2. An automatic chemical analyzing apparatus comprising:

means for successively transporting samples one by one in groups to a sampling station, said samples being grouped into a plurality of sample groups, each sample group including a plurality of samples which are to be analyzed with respect to the same test items;

means for successively feeding these transported samples, with each of these samples divided into a number of portions corresponding to the number of test items for the sample group which includes this sample, with a reagent to a reaction line;

means for discretely transporting through said reaction line the portions of the samples fed to said reaction line, respectively;

photometric means for optically measuring the portions of the samples transported through said reaction line and subjected to a reaction;

a central control unit for controlling operation timings of the transportation of the samples on said reaction line, the feeding of the samples to said reaction line, and the measuring operation of said photometric means, and for processing measured signals obtained from said photometric means; and item selection means for storing the test items for each sample group in a memory of said central control unit prior to the feeding of each sample group to said reaction line, wherein said central control unit controls the operation of said automatic chemical analyzing apparatus on the basis of test items read from said memory for another sample group when the samples of the sample group fed to said reaction line by said feeding means is changed to samples of said another sample group during the analyzing operation of said automatic chemical analyzing apparatus.

3. An apparatus according to claim 2, wherein said item selection means is provided with a plurality of item selection switches on an operation panel disposed on said apparatus, said switches being operated to store the test items in the memory of said central control unit.

4. An apparatus according to claim 3, further including means for altering the test item selected by any one of said item selection switches with another test item.

5. An apparatus according to claim 4, wherein said item altering means includes a group of item selecting switches disposed on said operation panel, said group of switches being operated to store working conditions of said apparatus required for test items to be newly set in areas of said memory corresponding to said item selection switches by which the items are altered.

6. An apparatus according to claim 3, wherein at least one of said item selection switches is constructed so as to store in said memory a combination of a plurality of test items.

7. An apparatus according to claim 2, wherein each test item for the plurality of sample groups is stored in said memory, and the test item is automatically changed each time that the sample group is changed.

8. An apparatus according to claim 2, further including means for reading a card on which a plurality of test items and working conditions for said apparatus required for each item are stored in codes, and for storing them in said memory.

9. An apparatus according to claim 8, wherein a plurality of cards storing thereon information with respect to different test items are prepared and changed to alter the test items.

10. An apparatus according to claim 2, further including means for reading a tape on which a plurality of test items and working conditions for said apparatus required for each test item are stored in codes, and for storing them in said memory.

11. An apparatus according to claim 2, wherein means is provided for sensing a boundary indicator disposed on a boundary between the sample groups each including the successive samples to transmit a sensing signal to said central control unit at a time when said boundary is sensed by said sensing means.

12. An automatic chemical analyzing method as in claim 1, wherein prior to feeding the first sample of a sample group to the reaction line, the photometrical measuring apparatus used for photometrically measuring the portions of the samples is automatically calibrated for each test item in that sample group.

13. An automatic chemical analyzing method as in claim 12, wherein the automatic calibration includes the steps of photometrically measuring, for each test item, a blank and a standard solution.

14. An automatic chemical analyzing apparatus as in claim 2, including means for automatically calibrating the photometric means for each test item in a sample group prior to feeding the first sample of that sample group to the reaction line.

15. An automatic chemical analyzing method as in claim 1, wherein the photometric measurement of the portions of the samples comprises shining a light beam through each of said portions onto a multiwavelength photometer, selecting the output from certain of a plurality of sensors which sense the wavelengths of the light from the photometer, said selecting being in accordance with instructions from the central control unit for each test item, and this output is then used to analyze each portion for that test item.

16. An automatic chemical analyzing apparatus as in claim 2, wherein the photometric means includes a multiwavelength photometer, means for producing a light beam to be shined through each of said portions and onto said photometer, a plurality of sensors for sensing the wavelengths of the light from the photometer, each of said sensors adapted to produce an output, and selecting means for selecting certain of said outputs in accordance with instructions from the central control unit for each test item, whereby these outputs can be used to analyze each portion for that test item.

* * * * *